$\|$ US007070983B2

(12) United States Patent
Ochi et al.

(10) Patent No.: US 7,070,983 B2
(45) Date of Patent: Jul. 4, 2006

(54) **MUTANT *PSEUDOMONAS PUTIDA* STRAINS AND METHODS OF USE THEREOF**

(75) Inventors: Kozo Ochi, Tsukuba (JP); Keiichi Hosokawa, Abiko (JP)

(73) Assignee: National Food Research Institute, Tsukuba (JP)

( * ) Notice: Subject to any disclaimer, the term of this patent is extended or adjusted under 35 U.S.C. 154(b) by 121 days.

(21) Appl. No.: 10/681,109

(22) Filed: Oct. 9, 2003

(65) Prior Publication Data

US 2005/0089989 A1   Apr. 28, 2005

(51) Int. Cl.
*C12N 1/20* (2006.01)
*C02F 3/34* (2006.01)
*B09C 1/10* (2006.01)

(52) U.S. Cl. ............... 435/253.3; 435/262; 435/262.5; 435/877

(58) Field of Classification Search ............. 435/253.3, 435/262, 262.5, 877
See application file for complete search history.

(56) References Cited

U.S. PATENT DOCUMENTS 5,948,671 A * 9/1999 Mazzola ................. 435/253.3
6,495,362 B1 * 12/2002 Nautiyal ................ 435/252.34

OTHER PUBLICATIONS

Rui Chen, et al., "Crystallization and Further Characterization of Meta-Hydroxybenzoate 4-Hydroxylase From Comamonas Testosteroni", Research Communications in Biochemistry, Cell and Molecular Biology, vol. 2, Nos. 3 & 4, (1998), pp. 253-274.
Sonja Isken, et al., "Bacteria Tolerant to Organic Solvents", Extremophiles, vol. 2, (1998), pp. 229-238.
Takayuki Nishijyo, et al., "the CbrA-CbrB two-component regulatory system controls the utilization of multiple carbon and nitrgoen sources in *Pseudomonas aeruginosa*", Molecular Microbiology, vol. 40, No. 4, (2001), pp. 917-931.
Joseph G. Leahy, et al., "Microbial Degradation of Hydrocarbons in the Environment", Microbiological Reviews, vol. 54, No. 3, Sep. 1990, pp. 305-315.
Robert Kuehberger, et al., "Alteration of Ribosomal Protein L6 in Gentamicin-Resistant Strains of *Escherichia coli*. Effects of Fidelity of Protein Synthesis", L6 Mutations Alter Ribosomal Ambiguilty, vol. 18, No. 1, (1979), pp. 187-193.
Akira Ishihama, et al., "Structural and Functional Modulation of *Escherichia coli* RNA Polymerase", Library of Congress Cataloging-in Publication Data, (1990), pp. 145-152.
Akira Inoue, et al., "A *Pseudomonas* thrives in high concentration of toluene"Nature, vol. 338, Mar. 16, 1989, pp. 264-266.
Mitchell Singer, et al., "Genetic Evidence for the Interaction between Cluster I and Cluster III Rifampicin Resistant Mutations", J. Mol. Biol. vol. 231, (1993), pp. 1-5.

David G. Thanassi, et al., Role of Outer Membrane Barrier in Efflux-Mediated Tetracycline Resistance of *Escherichia coli*, Journal of Bacteriology, vol. 177, No. 4, (Feb. 1995), pp. 998-1007.
Jan Sikkema, et al., "Mechanisms of Membrane Toxicity of Hydrocarbons", Microbiological Reviews, vol. 59, No. 2, (Jun. 1995), pp. 201-222.
Maria-Isabel Ramos-Gonzales, et al., "Physiological Characterization of *Pseudomonas putida* DOT-TIE Tolerance to p-Hydroxybenzoate", Applied and Environmental Microbiology, vol. 67, No. 9, (Sep. 2001), pp. 4338-4341.
Jan Roelop van der Meer, et al., "Molecular Mechanisms of Genetic Adaptation to Xenobiotic Compounds", Microbiological Reviews, vol. 56, No. 4, pp. 677-694.
Kenneth N. Timmis, "Designing Microorganisms for the Treatment of Toxic Wastes", Annu. Rev. Microbiol, vol. 48, (1994), pp. 525-557.
Frans J. Weber, et al., "Adaptation of *Pseudomonas putida* S12 to High Concentrations of Styrene and Other Organic Solvents", Applied and Environmental Microbioloty, vol. 59, No. 10, (Oct. 1993), pp. 3502-3504.
B.J. Wallace, et al., "Mechanism of Action of Antibacterial Agents", vol. 5/Part 1, (1979), pp. 272-303.
Norberto J. Palleroni, "The Prokaryotes, Second Edition", vol. 3, pp. 3071-3085.
Jeffery Vieira, et al., "Production of Single-Stranded Plasmid DNA", Methods in Enzymology, vol. 153, (1987), pp. 3-11.
Ding Jun Jin, et al., "Mapping and Sequencing of Mutations in the *Escherichia coli* rpoB Gene that Lead to Rifampicin Resistance", J. Mol. Biol., vol. 202, (1988), pp. 45-58.
Luca Comai, et al., "A New Technique for Genetic Engineering of *Agrobacterium* Ti Plasmid", Plasmid, vol. 10, (1983), pp. 21-30.
P. Buckel, et al. "Alteration of Ribosomal Protein L6 in Mutants of *Escherichia coli* Resistant to Gentamicin", Molec. Gen. Genet, vol. 158, (1977), pp. 47-54.
K. Ochi, et al., "Molecular and functional analysis of the ribosomal L11 and S12 protein genes (rplKl) and (rpsL) of *Streptomyces coelicolor* A3(2)", Mol Gen Genet, vol. 256, (1997), pp. 488-498.
J. Xu, et al., "A rifampicin resistance mutation in the rpoB gene confers ppGpp-independent antibiotic production in *Streptomyces coelicolor* A3(2)",Mol Genet Genomics, vol. 268, (2002), pp. 179-189.
Keiichi Hosokawa, et al. "Regulation of Synthesis of Early Enzymes of p-Hydroxybenzoate Pathway in *Pseudomonas putida*", vol. 245, No. 20, Issue of Oct. 25, 1970, pp. 5304-5308.
Jasper Kieboom, et al., "Identification and molecular characterization of an efflux system involved in *Pseudomonas putida* S12 mutidrug resistance", Microbiology, vol. 147, (2001), pp. 43-51.

(Continued)

*Primary Examiner*—Vera Afremova
(74) *Attorney, Agent, or Firm*—Oblon, Spivak, McClelland, Maier & Neustadt, P.C.

(57) ABSTRACT

The present invention relates to mutant strains of *Pseudomonas putida* and their use in the detoxification of industrial and/or toxic waste products.

15 Claims, 3 Drawing Sheets

OTHER PUBLICATIONS

The Journal of Antibiotics, "A Novel Method for Improving *Streptomyces coelicolor* A3(2) for Production of Actinorhodin by Introduction of rpsL (Encoding Ribosomal Protein S12) Mutations Conferring Resistance to *Streptomycin*", vol. 50, No. 6, Jun. 1997.

Marion Finken, et al., "Molecular basis of *Streptomycin* resistance in *Mycobacterium tuberculosis*: alterations of the ribosomal protein S12 gene and point mutations within a functional 16S ribosomal RNA pseudiknot", vol. 9, No. 6, (1993), pp. 1239-1246.

Haifeng Hu, et al., "Activation of Antibiotic Biosynthesis by Specified Mutations in the rpoB Gene (Encoding the RNA Polymerase βSubunit) of *Streptomyces lividans*", Journal of Bacteriology, vol. 184, No. 14, (Jul. 2002), pp. 3984-3991.

Takashi Inaoka, et al., "Construction of an In Vivo Nonsense Readthrough Assay System and Functional Analysis of Ribosomal Proteins S12, S4, and S5 in *Bacillus subtilis*", Journal of Bacteriology, vol. 183, No. 17, (Sep. 2001), pp. 4958-4963.

Hiroshi Nikaido "Multidrug Efflux Pumps of Gram-Negative Bacteria", Journal of Bacteriology, vol. 178, No. 20, (Oct. 1996), pp. 5853-5859.

Haifeng Hu, et al., "Novel Approach for Improving the Productivity of Antibiotic-Producing Strains by Inducing Combined Resistant Mutations", Applied and Environmental Microbiology, vol. 67, No. 4, (Apr. 2001), pp. 1885-1892.

G. Rasul Chaudhry, et al., "Biodegradation of Halogenated Organic Compounds", Microbiological Reviews, vol. 55, No. 1, (Mar. 1991), pp. 59-79.

M. A. Kertesz, et al., "Desulfurization and desulfonation: applications of sulfur-controlled gene expression in bacteria", Appl. Microbiol Biotechnol, vol. 57, (2001), pp. 460-466.

Abraham Esteve-Nunez, et al., "Biological Degradation of 2,4,6-Trinitrotoluene", Microbiology and Molecular Biology Reviews, vol. 65, No. 3, (Sep. 2001), pp. 335-352.

Eric Cundliffe, "Recognition Sites for Antibiotics within rRNA", (1990), pp. 479-490.

Teofila C. Beaman, et al., "Specificity and Control of Uptake of Purines and Other Compounds in *Bacillus subtitis*", vol. 156, No. 3, (Dec. 1983), pp. 1107-1117.

David G. Thanassi, et al., "Role of Outer Membrane Barrier in Efflux-Mediated Tetracycline Resistance of *Escherichia coli*", vol. 177, No. 4, (Feb. 1995), pp. 998-1007.

Kunihiko Nishino, et al., "Analysis of a Complete Library of Putative Drug Transporter Genes in *Escherichia coli*", vol. 183, No. 20, (Oct. 2001), pp. 5803-5812.

Jun Shima, et al., "Induction of Actinorhodin Production by rpsL (Encoding Ribosomal Protein S12) Mutations that Confer *Streptomycin* Resistance in *Streptomyces lividans* and *Streptomyces coelicolor* A3(2)", Journal of Bacteriology, vol. 178, No. 24, (Dec. 1996), pp. 7276-7284.

Caroline S. Harwood, et al., "Identification of the pcaRKF Gene Cluster from *Pseudomonas putida*: Involvement in Chemotaxis, Biodegradation, and Transport of 4-Hydroxybenzoate", Journal of Bacteriology, vol. 176, No. 21, (Nov. 1994), pp. 6474-6488.

Tomoyuki Mine, et al., "Expression in *Escherichia coli* of a New Multidrug Efflux Pump MexXY, from *Pseudomonas aeruginosa*", Antimicrobial Agents and Chemotherapy, vol. 43, No. 2, (Feb. 1999), pp. 415-417.

Rikizo Aono, et al., "Involvement of Outer Membrane Protein TolC, a Possible member of the *mar-sox* Regulan, in Maintenance and Improvement of Organic Solvent Tolerance of *Escherichia coli* K-12", Journal of Bacteriology, vol. 180, No. 4, (Feb. 1998), pp. 938-944.

Nadine Honore, et al., "*Streptomycin* Resistance in *Mycobacteria*", Antimicrobial Agents and Chemotherapy, vol. 38, No. 2, (Feb. 1994), pp. 238-242.

Juan L. Ramos, et al., "Isolation and Expansion of the Catabolic Potential of *Pseudomonas putida* Strain Able to Grow in the Presence of High Concentrations of Aromatic Hydrocarbons", Journal of Bacteriology, vol. 177, No. 14, (Jul. 1995), pp. 3911-3916.

Julio Ramos Aires, et al., "Involvement of an Active Efflux System in the Natural Resistance of *Pseudomonas aeruginosa* to Aminoglycosides", Antimicrobial Agents and Chemotherapy, vol. 43, No. 11, (Nov. 1999), pp. 2624-2628.

David G. White, et al., "Role of the acrAB Locus in Organic Solvent Tolerance mediated by Expression of marA, soxS, or robA in *Escherichia coli*", Journal of Bacteriology, vol. 179, No. 19, (Oct. 1997), pp. 6122-6126.

Antonia Rojas, et al., "three Efflux Pumps are Required to Provide Efficient Tolerance to Toluene in *Pseudomonas putida* DOT-T1E", Journal of Bacteriology, vol. 183, No. 13, (Jul. 2001), pp. 3967-3973.

Juan L. Ramos, et al., "Efflux Pumps Involved in Toluene Tolerance in *Pseudomonas putida* DOT-T1E", Journal of Bacteriology, vol. 180, No. 13, (Jul. 1998), pp. 3323-3329.

Kwag Kim, et al., "Isolation and Characterization of Toluene-Sensitive Mutants from the Toluene-Resistant Bacterium *Pseudomonas putida* GM73", Journal of Bacteriology, vol. 180, No. 14, (Jul. 1998), pp. 3692-3696.

Xian-Zhi Li, et al., "Role of the Multidrug Efflux Systems of *Pseudomonas aeruginosa* in Organic Solvent Tolerance", Journal of Bacteriology, vol. 180, No. 11, (Jun. 1998), pp. 2987-2991.

Thomas A. Wichelhaus, et al., "Molecular Characterization of rpoB Mutations Conferring Cross-Resistance to Rifamycins on Methicillin-Resistant *Staphylococcus aureus*", Antimicrobial Agents and Chemotherapy, vol. 43, No. 11, (Nov. 1999), pp. 2813-2816.

Albrecht Meier, et al., "Genetic Alterations in Streptomycin-Resistant *Mycobacterium tuberculosis*: Mapping of Mutations Conferring Resistance", Antimicrobial Agents and Chemotherapy, vol. 38, No. 2, (Feb. 1994), pp. 228-233.

Yoshiko Hosoya, et al., "Acquisition of Certain Streptomycin-Resistant (str) Mutations Enhances Antibiotic Production in Bacteria", Antimicrobial Agents and Chemotherapy, vol. 42, No. 8, (Aug. 1998), pp. 2041-2047.

Markus Heep, et al., "Rifampin and Rifabutin Resistance Mechanism in *Helicobacter pyloni*", Antimicrobial Agents and Chemotherapy, vol. 43, No. 6, (Jun. 1999), pp. 1497-1499.

Jasper Kieboom, et al., "Active Efflux of Organic Solvents by *Pseudomonas putida* S12 Is Induced by Solvents", Journal of Bacteriology, vol. 180, No. 24, (Dec. 1998), pp. 6769-6772.

Keiichi Hosokawa, et al., "Streptomycin-resistant (rpsLI) or rifampicin-resistant (rpoB) mutation in *Pseudomonas putida* KH146-2 confers enhanced tolerance to organic chemicals", Environmental Microbiology (2002) 4(11), pp. 703-712.

N. Tamchiro, et al., "Innovative Approach for Improvement of an Antibiotic-Overproducing Industrial Strain of *Streptomyces albus*", Applied and Environmental Microbiology, Nov. 2003, vol. 69, No. 11, pp. 6412-6417.

Maria-Jose Huertas, et al., "Tolerance to Sudden Organic Solvent Shocks by Soil Bacteria and Characterization of Pseudomonas putida Strains Isolated from Toluene Polluted Sites," Environ. Sci. Technol., 2000, vol. 34, No. 16, pp. 3395-3400.

* cited by examiner

MUTANT *PSEUDOMONAS PUTIDA* STRAINS AND METHODS OF USE THEREOF

BACKGROUND OF THE INVENTION

1. Field of the Invention

The present invention relates to mutant strains of *Pseudomonas putida* and their use in the detoxification of industrial and/or toxic waste products.

2. Description of the Background

Many organic compounds synthesized from petroleum and other chemicals are highly toxic and recalcitrant. Herbicides, insecticides, chlorosubstituted dioxins and PCBs are known biohazardous compounds. Therefore, environmental protection efforts have been focussed on the development of more effective processes for the treatment of these toxic wastes.

Microorganisms used to process these hazardous wastes are likely to be exposed to a wide range of waste concentrations. Thus, this is one of the first problem that must be faced when addressing biological waste treatment issues. Above a certain threshold, toxic chemicals can kill a community of microorganism. Therefore, it is intrinsically important to confer a higher tolerance for waste chemicals, as pointed out by Timmis et al. ((1994) *Annu Rev Microbiol* 48:525–557). Soil bacteria has a wide range of metabolic abilities which make it a useful tool for mineralization of toxic compounds (reviewed by Chaudhry and Chapalamadugu, ((1991) *Microbiol Rev* 55: 59–79); Esteve-Nunez et al., ((2001) *Microbiol Mol Biol Rev* 65: 335–352); Kertesz and Wietek, ((2001) *Appl Microbiol Biotechnol* 57:460–466); Leahy and Colwell, ((1990) *Microbiol Rev* 54:305–315); Timmis et al., ((1994) *Annu Rev Microbiol* 48:525–557); Van der Meer et al., ((1992) *Microbiol Rev* 56:677–694)).

*Pseudomonas* is a major aerobic microorganism which can mineralize various organic compounds in environment. The greatest number of strains shown to be tolerant to organic chemicals belong to this genus (Inoue and Horikoshi, ((1989) *Nature,* 388:264–266); Kim et al., ((1998) *Pseudomonas putida* GM73 *J Bacteriol* 180:3692–3696); Ramos et al., ((1998) *J Bacteriol* 180:3323–3329); Weber et al., ((1993) *Appl Environ Microbiol* 59:3502–3504)). A single species of *Pseudomonas* as well as *Comamonas* is capable of growth on more than 80 organic compounds as a sole source of carbon and energy (reviewed by Palleroni, (1992) Introduction to the family *Pseudomonadaceae*. In *the prokaryotes. A handbook on the biology of bacteria: ecophysiology, isolation, identification, applications. Vol. 3* Balows, A., Trüper, H. G., Dworkin, M., Harder, W., and Schleifer, K.-H. (eds.) Springer-Verlag, New York. pp. 3071–3085). The pathways for metabolizing those compounds are highly specific and complex. Most of the enzymes in these catabolic pathways are known to be inducible (Chen et al., (1998) *Res Communs Biochem and Cell & Mol Biol* 2: 253–274). The discovery of microorganisms capable of tolerating to, or growing on, high concentrations of organic solvents provides a potentially interesting avenue for development of genetically engineered organisms for treating hazardous wastes. Solvent-resistance is inheritable and can be generated by random mutagenesis, and thus appears to be a useful phenotype for waste processing (reviewed by Timmis et al., (1994) *Annu Rev Microbiol* 48:525–557). Therefore, development of genetically enhanced microorganisms, through the use of genetic engineering, is important for developing better biological waste processing technologies.

In previous work (Hesketh and Ochi, ((1997) *J Antibiot* 50:532–535); Hosoya et al., ((1998) *Antimirob Agents Chemother* 42:204–2047); Hu and Ochi, ((2001) *Appl Environ Microbiol* 67:1885–1892)), we have demonstrated that the secondary metabolism of the genera *Streptomyces* and *Bacillus* (i.e. antibiotic production) could be activated or enhanced dramatically by introducing a mutation that confers resistance to streptomycin, gentamicin or rifampicin. These mutants have a mutation in the gene which encodes the ribosomal protein S12 (in Str mutants) or the RNA polymerase β-subunit (in Rif mutants) (Hu et al., ((2002) *J Bacteriol* 184: 3984–3991); Inaoka et al., ((2001) *J Bacteriol* 183:4958–4963); Ochi et al., ((1997) *Mol Gen Genet* 256:488–498); Shima et al., ((1996) *J Bacterial* 178:7276–7284); Xu et al., (2002) *Mol Genet Genom*, in press)).

In view of the damaging effects that toxic and industrial wastes pose to the environment and human health there remains a need for improved ways to detoxify these wastes.

SUMMARY OF THE INVENTION

Accordingly, one object of the present invention is to provide methods for increasing the tolerance of *Pseudomonas putida* strains to organic substances, e.g., that are toxic.

Another object of the present invention is to provide novel strains of *Pseudomonas putida* that have increased tolerance to toxic organic compounds.

In addition, by providing such strains, the invention aims to provide improved methods of treating toxic organic compounds, such as those found in industrial waste with these *Pseudomonas putida* strains.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The present inventors found that certain Str-, Gen- and/or Rif-mutants derived from *Pseudomonas putida*, such as *Peudomonas putida* KH146-2, which are resistant to streptomycin, gentamicin and/or rifampicin respectively, are tolerant to the aromatic compound 4-hydroxybenzoate (4HBA). In addition to or independent from the Str-, Gen- and/or Rif-mutants, the *Peudomonas putida* strains may also be resistant to other antibiotics as well, for example, fusidic acid, thiostrepton, tetracycline, and others.

The minimum inhibitory concentration (MIC) of 4HBA as the sole carbon source for the wild-type strain was 1%, while the MIC for the mutants was 1.7%. Frequency of 4HBA-tolerant mutants among spontaneous Str-, Gen- and Rif-mutants was 5–15%, 3%, and 3–5%, respectively. These 4HBA-tolerant mutants also tolerated to a variety of organic chemicals such as 3-hydroxybenzoate, aliphatic and heterocyclic compounds, chlorobenzoates, as well as organic solvents toluene and m-xylene.

In view of these findings, the present invention provides methods for increasing the tolerance of *Pseudomonas putida*, such as *Peudomonas putida* KH146-2, to organic substances, e.g., toxic organic substances. The method involves growing a *Pseudomonas putida* strain, which is resistant to one or more antibiotics such as streptomycin, gentamicin, rifampicin, fusidic acid, thiostrepton, tetracycline, and others, in a media using one or more organic substances as the sole carbon source. Obtaining the strains that are resistant to one or more antibiotics can be carried out in a conventional manner which includes growing the strain on a medium containing the one or more antibiotics and isolating those colonies that grow.

Examples of those organic substances include, benzoate and benzoate derivatives, such as 2-hydroxybenzoate, 3-hydroxybenzoate, 4, hydroxybenzoate, cholorobenzoates (including, for example, 2-chlorobenzoate, 3-chlorobenzoate, 4-chlorobenzoate, 2,3-dichlorobenzoate, 2,4-dichlorobenzoate, 4-chlorosalicylate), fluorobenzoate, (including, for example, 2-fluorobenzoate, 3-fluorobenzoate), toluene and toluene derivative, benzene and benzene derivatives, aliphatic compounds, heterocyclic compounds, xylene and xylene derivatives. Other examples include herbicides, insecticides, chlorosubstituted dioxins, and PCBs.

To isolate those *Pseudomonas putida* that have increased tolerance to the organic substance, the strain is cultured in an appropriate medium using the organic substance as the carbon source at increasing concentrations of the organic substance for a period of time that results in the growth of colonies plated on the medium. The initial starting concentration is about 0.8% whereby colonies that grow are transferred to another culture medium containing increasing concentrations by increments of about 1% until a final concentration is about 5%.

As used herein, *Pseudomonas putida* strains with increased tolerance to organic substances means increased relative to the *Pseudomonas putida* strain prior to subjecting it to the method described herein.

The Str mutants had a point mutation in the rpsL gene, which produces the ribosomal protein S12.

The Rif mutants were found to have a point mutation in the rpoB gene, which encodes the RNA polymerase β-subunit. Mutation points in Gen mutants still remain unknown. Str-, Gen-, and Rif-phenotypes occurred in spontaneous 4HBA-tolerant mutants which had been selected by successively increasing concentrations (from 0.8% to 5%) of 4HBA. Complementation experiments with one of the Str mutants demonstrated a causal relationship between a rpsL mutation (str-1) and 4HBA tolerance. Uptake experiments using [$^{14}$C]4HBA revealed that apparent ability of 4HBA to be taken up by the membrane transport system was reduced 2 to 3-fold in the mutants compared to the wild-type strain, accounting at least partly for the enhanced tolerance to 4HBA.

Thus, *Pseudomonas putida* strains having Arginine in place of Lysine at position 88 in the ribosomal S12 protein and/or mutations in the RNA polymerase β subunit. The sequences of ribosomal protein S12 of *Pseudomonas putida* are known, for example, see GenBank entries NP742615 and AAN66079.1. The RNA polymerase β subunit sequences from *Pseudomonas putida* are also known, for example, see GenBank entries P19175 and 19176.

Preferred examples of *Pseudomonas putida* strains are Str-mutants of *Pseudomonas putida* no. 3, Gen-mutant of *Pseudomonas putida* no. 12, Rif-mutant of *Pseudomonas putida* no. 17; and Str- and Gen-double mutant of *Pseudomonas putida* no. 55, these strains are deposited at the International Patent Organism Depository, National Institute of Advanced Industrial Science and Technology at AIST Tsukuba Central 6, 1—1, Higashi 1-Chome, Tsukuba-shi, Ibaraki-ken 305-8566, Japan and assigned the following Accession numbers:

*Pseudomonas putida* strain no. 3—FERM BP-08462
*Pseudomonas putida* strain no. 12—FERM BP-08463
*Pseudomonas putida* strain no. 17—FERM BP-08464
*Pseudomonas putida* strain no. 55—FERM BP-08465

The *Pseudomonas putida* strains can be admixed with one or more suitable carriers individually or together with one or more *Pseudomonas putida* strain and/or other bacterial strains as described herein.

The *Pseudomonas putida* strains described herein can be used to detoxify in whole, or in part, materials containing toxic substances and/or industrial wastes containing such toxic substances. Examples of toxic substances include, benzoate and benzoate derivatives, such as 2-hydroxybenzoate, 3-hydroxybenzoate, 4, hydroxybenzoate, cholorobenzoates (including, for example, 2-chlorobenzoate, 3-chlorobenzoate, 4-chlorobenzoate, 2,3-dichlorobenzoate, 2,4-dichlorobenzoate, 4-chlorosalicylate), fluorobenzoate, (including, for example, 2-fluorobenzoate, 3-fluorobenzoate), toluene and toluene derivative, benzene and benzene derivatives, aliphatic compounds, heterocyclic compounds, xylene and xylene derivatives. Other examples include herbicides, insecticides, chlorosubstituted dioxins, and PCBs.

Sources of toxic and/or industrial waste to be treated are generally known and include, waste receptacles in industrial plants, waste receptacles at an approved or non-approved disposal site, ground water, bodies of water, such as lakes, streams, rivers and the like, soil, household or commercial sources of toxic wastes derived from various cleaning solutions, solvents and the like.

To treat the toxic and/or industrial waste, the *Pseudomonas* strains described herein are brought in contact with these wastes in amounts and for a time such that a partial or complete degradation of the toxic substances is effectuated. To detoxify waste effectively, it is possible to adjust the concentration of the waste to the upper limit, to which organisms are tolerant for growth. In the case of 4HBA detoxification by *Pseudomonas putida*, the preferable concentration of 4HBA is 2%. Also, two to three times treatment is preferable for complete degradation of the toxic substance.

In so treating these wastes, various combinations of the *Pseudomonas* strains can be employed. Likewise, other bacterial strains in the Pseudomonocae family may also be combined, such as, *Commamonas* sp., e.g., *Commamonas testeroni*. In addition to *Pseudomonas* and *Commamonas*, combination with other bacteria such as *Rhodococcus* may be effective to enhance the ability of detoxification.

A single bacterial strain or mixtures of bacterial strains can be provided as a composition with additional appropriate carriers, such as the media used for growth, water, buffered solutions, etc.

EXAMPLES

Experimental Procedures

Bacterial Strains, Growth Conditions, and Isolation of Mutants

*Pseudomonas putida* KH146-2 was originally isolated from soil for the capability of growing in the presence of 4-hydroxybenzoate (Chen et al., ((1998) *Res Communs Biochem and Cell & Mol Biol* 2: 253–274)). HBM medium consists of 50 mM sodium potassium phosphate buffer (pH6.8), 0.1% $(NH_4)_2SO_4$ and Hutner's base. Hutner's base cotained (per liter) nitrilotriacetic acid, 200 mg; $CaCl_2.2H_2O$, 67 mg; $(NH_4)_6Mo_7O_{24}.4H_2O$, 185 µg; $MgSO_4$, 289 mg; EDTA, 2.5 mg; $ZnSO_4.7H_2O$, 11 mg; $FeSO_4.7H_2O$, 7 mg; $MnSO_4.H_2O$, 1.5 mg; $CuSO_4.5H_2O$, 390 µg; $Co(NO_3)_2.6H_2O$, 250 µg, and $Na_2B_4O_7.10H_2O$, 180 µg. LB medium contains 1% tryptone, 0.5% yeast extract, and 1% NaCl (adjusted pH 6.8). LBH medium contains 1% tryptone and 0.5% yeast extract in HBM medium. The bacteria were grown at 30° C. in a shaker at 200 rpm. For tolerance tests, HBM or LBH agar plates containing serially increasing concentrations of an organic chemical were employed. Routinely, 20 to 40 bacterial strains were spot-transplanted with the aid of tooth pick on an agar plate, followed by incubation at 30° C. for 3 days. The lowest concentration in % of an organic chemical that totally inhibits growth was defined as the minimum inhibitory concentration (MIC).

Spontaneous streptomycin-resistant (Str), gentamicin-resistant (Gen) or rifampicin-resistant (Rif) mutants were obtained from colonies that grew within 3 days after wild-type cells were spread on LB agar containing various concentrations of antibiotic.

Isolation of 4HBA Tolerant Mutants by Adaptation

Wild-type strain KH146-2 was adapted, step by step, to grow in HBM medium containing increasing concentrations (from 0.8% to 5%) of 4HBA. In steps using high concentrations (>3%) of 4HBA, adaptation required a longer term incubation (7~10 days) for each step. In certain steps, the 4HBA-adapted mutants were isolated using agar plates (containing the adapted concentrations of 4HBA), on which tolerant mutants formed big size colonies.

Mutation Analysis of the rpsL, rplF and rpoB Genes

The rpsL gene fragment in a Str mutant was obtained by PCR using the mutant genomic DNA as a template and synthetic oligo-nucleotide primers P1 (forward: 5'-CGTAA-GACAATCAGTGGAGC-3'-SEQ ID NO:1) and P2 (reverse: 5'-CCGACCTTACTCTTATCGAC-3'-SEQ ID NO:2) which were designed from the sequence of *P. aeruginosa* PA01 (PathoGenesis annotation no. PA268). Similarly, the rplF gene in a Gen mutant was obtained using primers P3 (foward: 5'-AAGAACCCCGTCAAGCTCC-3'-SEQ ID NO:3) and P4 (reverse: 5'-TCTTTACGACGGAC-GACTTC-3'-SEQ ID NO:4). PCRs were performed with Taq polymerase (Takara Ex-Taq) following the manufacturer's instructions. A Perkin-Elmer Cetus thermal cycler was used, and conditions were as follows: 5 min of incubation at 94° C., followed by 30 cycles of 94° C. for 0.3 min, 55° C. for 0.3 min, 72° C. for 0.3 min, and finally at 72° C. for 5 min. PCR products were directly sequenced by the dideoxy chain-termination procedure using the Big Dye Terminator Cycle Sequencing kit (Perkin-Elmer Applied Biosystems, Foster City, Calif.). The sequence data were analyzed with the GENETIX program (Software Development, Tokyo). The partial rpoB gene fragment (nt. 1524 to 2159) of the Rif mutant was obtained by PCR using a mutant genomic DNA as a template and synthetic oligo-nucleotide primers P5 (forward:5'-TGATCAACGCCAAGCCGGT-3'-SEQ ID NO:5) and P6 (reverse: 5'-TTGCGCTCCATGCCGGTAC-3'-SEQ ID NO:6) which were designed from the *P. putida* sequence (DBGET accession No. X15846). The PCR method and DNA sequencing are the same as those described for the rpsL and rplF genes.

Cloning of rpsL for Complementation Tests

To clone the rpsL gene, a 0.9-kb DNA region covering whole rpsL was amplified from the chromosomal DNA of *P. putida* KH146-2 using KDO DNA polymerase (Toyobo Biochemicals, Osaka). Oligonucleotide primers were designed according to the rpoC-rpsL-rpsG sequence of *P. putida* KT2440 (www.tigr.org); 5'-CGTTTTGCCGCTA-CACGACGTCTTGGCAT-3' (SEQ ID NO:7—nucleotides [nt]–368 to –341 upstream of rpsL) and 5'-AA-GAGAACGTGGTCGTGGGTCGTCTGATC-3' (SEQ ID NO:8—complementary to nt 107 to 135 downstream of rpsL). The amplified DNA fragments were cloned into plasmid pUC118 (Vieira and Messing, (1987) *Methods Enzymol* 153: 3–11) to confirm the sequence, then excised from the plasmids as a BamHI-SphI fragment using the restriction sites in the multi-cloning sequence of the vector and inserted between the BglII and SphI sites of the *E. coli*-*Pseudomonas* shuttle vector pNIT6010 carrying $tet^R$, a derivative of pNIT6011 (Nishijyo et al. (2001) *Mol Microbiol* 40:917–931). The resultant plasmid pYI433, as well as vector control pNIT6010, was introduced into the Str mutant no. 3 (str-1) by conjugation using *E. coli* HB101/pRK2013 as the helper (Comai et al. (1983) *Plasmid* 10:21–30). Fifty µg $ml^{-1}$ of tetracycline was used for selection of transformants.

Assay for the Aromatic Compounds

Aromatic compounds were assayed using the Hitachi Lachrom HPLC with a cap cell pack C18 UG 1205-5 column (4.6 mm×15 mm; Shiseido, Tokyo) at a flow rate of 1 ml $min^{-1}$ with a mobile phase ($CH_3CN:H_2O=30:70$, adjusted to pH 2.5 with trifluoroacetic acid). Detection for 4HBA was done using a UV detector set at 230 nm. 4HBA was eluted at 4.25 min.

Measurement of Uptake of 4HBA

The method described by Thanassi et al. ((1995) *J Bacteriol* 177:998–1007) was used with some modifications. The bacteria were grown to mid-log phase in HBM medium containing 0.3% 4HBA, washed and resuspended in 0.3% succinate-HBM medium to give $OD_{660}$=0.7. A 5 ml-aliquot of the bacterial suspension in a 100 ml flask was incubated in a shaker bath. A 0.5 µCi [carboxyl-$^{14}$C]4HBA (55 mCi $mmol^{-1}$, ARC.) with unlabelled 4HBA at increasing concentrations, were added to the 5 ml bacterial suspension and incubation was continued. At the indicated time, a 0.5 ml aliquot of sample was removed and filtered using a nitrocellulose filter (0.45 μm pore size, Millipore Corp, Bedford, Mass.) which had previously been washed with 2 ml of HBM medium containing 5 mM 4HBA. The sample was applied with a Pipetman, followed by immediate washing with 3 ml of 5 mM 4HBA-HBM medium. The membrane filter was dried, and transferred to a scintillation vial containing Brey's solution, and radioactivity was measured in scintillation spectrometer. From the rate of uptake and the concentration of 4HBA, apparent Km was determined by reciprocal plotting as described by Beman et al ((1983) *J Bacteriol* 156:1107–1117).

Determination of Protein Synthesis

Strains were grown to mid-log phase ($OD_{660}=0.7$) in 0.3% succinate-HBM medium. A 5 ml aliquot was transferred to each of three 100 ml flasks. [$^{14}C(u)$]Leucine (300 mCi mmol$^{-1}$, NEN) and unlabelled leucine were then added to each flask to give a final concentration of 0.1 μCi ml$^{-1}$ and 100 μM, respectively. At the same time, 4HBA was added to give a final concentration of 0.6% or 1.2% to two of the three flasks. At time zero and at the indicated times thereafter, a 475 μl-aliquot was transferred to an Eppendorf tube which contained 25 μl of 100% TCA with 100 mM unlabelled leucine. The resulting 5% TCA mixture was left in an ice-water bath for 30 min and then filtered through a nitrocellulose membrane filter. The filter was washed with 5 ml of 5% TCA containing 5 mM leucine (to chase membrane-bound labelled leucine), dried and radioactivity was counted using scintillation spectrometer.

RESULTS

Occurrence of the 4HBA Tolerance Phenotype Among Antibiotic-Resistant Mutants

We first isolated a number of spontaneous streptomycin-resistant (Str), gentamicin-resistant (Gen) and rifampicin-resistant (Rif) mutants of *P. putida* KH146-2. These mutants appeared at a frequency of $10^{-5}$–$10^{-6}$ when KH146-2 cells were spread on LB agar containing various amounts of antibiotics. [Growth of parental strain KH146-2 was completely suppressed with 100 μg ml$^{-1}$ of streptomycin, 12 μg ml$^{-1}$ of gentamicin, or 10 μg ml$^{-1}$ of rifampicin]. Forty mutants resistant to each antibiotic were randomly selected and examined for tolerance to 4-hydroxybenzoic acid (4HBA). 4HBA-tolerant strains, which could grow in the presence of 1% 4HBA, were detected among these antibiotic resistant mutants at a high frequency of 3 to 15% (Table 1). The highest frequency (15%) was detected in the mutants selected with 1000 μg ml$^{-1}$ of streptomycin. These 4HBA-tolerant isolates all grew as well as the parent strain on LB agar.

TABLE 1

Occurrence of 4HBA tolerant mutants among antibiotic resistant isolates of *P. putida*

| Str, Gen, or Rif mutants | Concn of antibiotic used for selecting (μg ml$^{-1}$) | Frequency of 4HBA tolerant isolates[a] |
|---|---|---|
| Streptomycin | 500 | 2/40 (5%) |
| Streptomycin | 1000 | 6/40 (15%) |
| Gentamicin | 20 | 1/40 (3%) |
| Rifampicin | 20 | 2/40 (5%) |
| Rifampicin | 50 | 1/40 (3%) |

[a]Forty mutant strains were spot-transplanted onto HBM agar plates containing 1% 4HBA (as a sole carbon source) and incubated at 30° C. Growth was determined after 6 days incubation.

Tolerance to Various Organic Compounds

Using several strains randomly chosen as representatives of 4HBA-tolerant mutants, we examined the tolerance level to various organic compounds. As summarized in Table 2, the Str mutants and Rif mutants tested all revealed a modest increment of tolerance to 3HBA and to two chlorine-substituted benzoate isomers, 4-chlorobenzoate (4CB) and 2-chlorobenzoate (2CB). However, slight or no increase of tolerance was detected for 2-hydroxybenzoate (2HBA), 3-chlorobenzoate (3CB) and benzoic acid (BA). Tolerance levels to other organic compounds were also examined. We could detect increased tolerance of the Str and Rif mutants to fatty acids (isobutyrate, norvalerate and isovalerate), a heterocyclic compound (isonicotinate), and halogen-substituted benzoate derivatives (4-fluorobenzoate, 2-iodobenzoate, 3-iodobenzoate, 3-bromo-4-hydroxybenzoate, 4-chlorosalicylate and 5-chlorosalicylate) (data not shown).

TABLE 2

Tolerance (MIC) of *P. putida* mutant strains to benzoate and its derivatives

| Strain no. | Concn of antibiotic used for selecting the mutants (μg ml$^{-1}$)[a] | Benzoate and its derivatives in LBH medium[b] | | | | | | |
|---|---|---|---|---|---|---|---|---|
| | | 4HBA | 3HBA | 2HBA | 4CB | 3CB | 2CB | BA |
| Wild-type | | 1.4 ± 0.1 (1.1 ± 0.1)[c] | 1.4 ± 0.1 | 0.8 ± 0.1 | 1.4 ± 0.1 | 0.9 ± 0.1 | 1.5 ± 0.2 | 0.8 ± 0.2 |
| 3 | 1000 (STR) | 1.9 ± 0.1 (1.7 ± 0.1) | 1.8 ± 0.2 | 0.9 ± 0.1 | 1.7 ± 0.1 | 1.1 ± 0.2 | 1.9 ± 0.2 | 1.0 ± 0.1 |
| 9 | 500 (STR) | 1.6 ± 0.2 (1.3 ± 0.2) | 1.8 ± 0.1 | 0.8 ± 0.1 | 1.7 ± 0.1 | 1.0 ± 0.2 | 1.7 ± 0.2 | 0.9 ± 0.1 |
| 12 | 20 (Gen) | 1.9 ± 0.3 (1.6 ± 0.2) | 1.9 ± 0.2 | 0.8 ± 0.1 | 1.6 ± 0.2 | 1.1 ± 0.2 | 1.9 ± 0.3 | 1.0 ± 0.1 |
| 14 | 50 (RIF) | 1.8 ± 0.2 (1.4 ± 0.2) | 1.9 ± 0.1 | 0.8 ± 0.1 | 1.8 ± 0.2 | 1.3 ± 0.2 | 1.9 ± 0.2 | 1.1 ± 0.1 |
| 15 | 20 (RIF) | 1.8 ± 0.2 (1.2 ± 0.2) | 1.9 ± 0.2 | 0.8 ± 0.1 | 1.8 ± 0.1 | 1.3 ± 0.2 | 2.0 ± 0.2 | 1.0 ± 0.1 |
| 17 | 20 (RIF) | 1.8 ± 0.2 (1.3 ± 0.1) | 1.8 ± 0.3 | 0.7 ± 0.1 | 1.7 ± 0.1 | 1.2 ± 0.1 | 2.1 ± 0.2 | 1.1 ± 0.1 |
| 18 | 20 (RIF) | 2.0 ± 0.2 (ND[d]) | ND | ND | ND | ND | ND | ND |

TABLE 2-continued

Tolerance (MIC) of *P. putida* mutant strains to benzoate and its derivatives

| | Concn of antibiotic used for selecting the mutants | Benzoate and its derivatives in LBH medium[b] | | | | | | |
|---|---|---|---|---|---|---|---|---|
| Strain no. | (μg ml$^{-1}$)[a] | 4HBA | 3HBA | 2HBA | 4CB | 3CB | 2CB | BA |
| 20 | 20 (RIF) | 1.9 ± 0.1 (ND) | ND | ND | ND | ND | ND | ND |

[a]STR, GEN, and RIF denote streptomycin, gentamicin, and rifampicin, respectively.
[b]Abbreviations: 2HBA, 3HBA, and 4HBA denote 2-, 3-, and 4-hydroxybenzoate, respectively. BA indicates benzoate. 2CB, 3CB, and 4CB stand for 2-, 3-, and 4-chlorobenzoate, respectively.
[c]The mean value of two to four separate experiments is indicated with the standard deviation. MIC values detected using HBM medium containing 4HBA as a sole carbon source are presented in parentheses.
[d]ND, not determined.

We then examined whether Str and Rif mutants exhibit an increased tolerance to organic solvents such as toluene and xylene. The growth of KH146-2 was inhibited almost completely in LBH medium containing saturated concentrations of m-xylene, while Str and Rif mutants grew in this medium. Likewise, growth of KH146-2 was somewhat retarded in 3% MeOH-LBH medium saturated with toluene, but these mutants grew normally indicating correlation of Str and Rif mutations with organic solvent tolerance (data not shown).

Mutational Analyses of the Mutants

Streptomycin resistance frequently results from a mutation in the rpsL gene for the ribosomal protein S12 (Hosoya et al., ((1998) *Antimirob Agents Chemother* 42:204–2047); Inaoka et al., ((2001) *J Bacteriol* 183:4958–4963); Shima et al., ((1996) *J Bacterial* 178:7276–7284)). Rifampicin resistance results from a mutation in the rpoB gene (β-subunit of RNA polymerase) (Heep et al., ((1999) *Antimicrob Agents Chemother* 43:1497–1499); Jin and Gross, ((1988) *J Mol Biol* 202:45–58); Wichelhaus et al., ((1999) *Antimicrob Agents Chemother* 43:2813–2816); Hu et al., ((2002) *J Bacteriol* 184: 3984–3991)). We therefore sequenced and compared the rpsL gene and rpoB gene from the mutants to the wild-type strain. As summarized in Table 3, the eight Str mutants with increased tolerance to 4HBA all contained a mutation in rpsL gene at position 263 or 128 resulting in an alteration of Lys-88 to Arg or Lys-43 to Arg, respectively. It is notable that the level of resistance to streptomycin was extremely high (>100 mg ml$^{-1}$), displaying more than a 1000-fold resistance compared to the wild-type strain (Table 3). Most of the str mutants (except for strain no. 9), which were tolerant to 4HBA, had the same mutation which altered Lys-88 to Arg. Although gentamicin, like streptomycin, is classified as an aminoglycoside antibiotic, the three Gen mutants tested had no mutation in the rpsL gene (Table 3). Also, no mutation was detected in the rplF gene coding for ribosomal L6 protein (data not shown).

TABLE 3

Summary of mutations on the *P. putida* genes resulting in tolerance to 4HBA

| Strain no. | Relevant genotype | Mutated gene | Nucleotide exchange[a] | Amino acid exchange | Resistance level (μg ml$^{-1}$) to antibiotic[b] |
|---|---|---|---|---|---|
| 2 | str-1 | rpsL | 263A→G | Lys88→Arg | >100,000 (STR) |
| 3 | str-1 | rpsL | 263A→G | Lys88→Arg | >100,000 (STR) |
| 4 | str-1 | rpsL | 263A→G | Lys88→Arg | >100,000 (STR) |
| 5 | str-1 | rpsL | 263A→G | Lys88→Arg | >100,000 (STR) |
| 6 | str-1 | rpsL | 263A→G | Lys88→Arg | >100,000 (STR) |
| 8 | str-1 | rpsL | 263A→G | Lys88→Arg | >100,000 (STR) |
| 9 | str-2 | rpsL | 128A→G | Lys43→Arg | >100,000 (STR) |
| 10 | str-1 | rpsL | 263A→G | Lys88→Arg | >100,000 (STR) |
| 11 | gen | —[c] | | | 50 (GEN) |
| 12 | gen | — | | | 50 (GEN) |
| 13 | gen | — | | | 50 (GEN) |
| 14 | rif-1 | rpoB | 1730T→C | Ile577→Thr | >500 (RIF) |
| 15 | rif-2 | rpoB | 1549T→C | Ser517→Pro | >500 (RIF) |
| 17 | rif-3 | rpoB | 1562A→G | Asp521→Gly | 500 (RIF) |
| 18 | rif-4 | rpoB | 1553A→G | Gln518→Arg | 500 (RIF) |
| 19 | rif-5 | rpoB | 1561G→A | Asp521→Asn | 500 (RIF) |
| 20 | rif-5 | rpoB | 1561G→A | Asp521→Asn | 500 (RIF) |
| 21 | rif-3 | rpoB | 1562A→G | Asp521→Gly | 500 (RIF) |
| 22 | rif-3 | rpoB | 1562A→G | Asp521→Gly | 500 (RIF) |
| 23 | rif-4 | rpoB | 1553A→G | Gln518→Arg | 500 (RIF) |
| 24 | rif-4 | rpoB | 1553A→G | Gln518→Arg | 500 (RIF) |

[a]Numbering originates from the start codon of the open reading frame.
[b]Determined after 1 days of cultivation on LB agar. STR, GEN, and RIF denotes streptomycin, gentamicin, and rifampicin, respectively.
[c]Mutations were not detected within the rpsL gene.

In sequencing the rpoB gene of the Rif mutants, we focused on a specific region (nt 600 to 1300) corresponding to the Rif domain of *E. coli* (Jin and Gross, (1988) *J Mol Biol* 202:45–58). The sequencing data obtained for the Rif mutants revealed that all possess a point mutation in the Rif region (Table 3). Thus, the Str mutants and Rif mutants with increased tolerance to 4HBA were found to be tightly linked with the mutations in rpsL and rpoB genes, respectively. When Str mutants were first selected for resistance to streptomycin, followed by rpsL sequencing, these sequenced rpsL mutants (we tested eleven str-1 mutants and seven str-2 mutants) all revealed resistance to 4HBA, suggesting a causal relationship between the str mutations and 4HBA tolerance.

Str Gen double mutants all possessed a mutation within rpsL, which altered Lys-88 to Arg, but no mutation was detected in the rplF gene. These results strongly implicate the intrinsic role of Str, Gen and Rif traits in developing a tolerance to 4HBA. Strain no. 55 (FERM BP-08465) was used for further study as a representative of Str Gen double mutants.

Strain no. 55 as well as other Str Gen double mutants no longer grew on a 5% 4HBA-containing medium (but still showed a tolerance to 3% 4HBA) when strains were grown once on LB medium without 4HBA. This indicates that the cell's physiological changes besides genetic mutations took part in the high-level (5% 4HBA) tolerance.

TABLE 4

Occurrence of antibiotic resistant traits in 4HBA tolerant mutants from *P. putida*

| Concn (%) of 4HBA used for accumulating the 4HBA tolerant mutants[a] | Number of 4HBA tolerant isolates examined | Frequency of isolates resistant to: | | |
|---|---|---|---|---|
| | | Streptomycin (500 μg ml$^{-1}$) | Gentamicin (20 μg ml$^{-1}$) | Rifampicin (25 μg ml$^{-1}$) |
| 0.8→1.4→1.8→2.6→2.9 | 84 | 6 (7%) | 11 (13%) | 10 (12%) |
| 2.9→3.4→3.7→4.0→4.3 | 40 | 3 (8%) | 10 (25%) | 3 (8%) |
| 4.3→4.7→5 | 16 | 16 (100%) | 16 (100%) | 0 |

[a]The wild-type strain *P. putida* KH146-2 was adapted to grow in liquid medium which contains stepwise-increasing (0.8%→5% concentrations of 4-HBA as described in Experimental procedures. During the course of growth adaptation, tolerant mutants were isolated and tested for antibiotic resistance.

Complementation Experiments for str-1 Mutation

We demonstrated further the casual relationship between the str-1 mutation and 4HBA-tolerance by complementation experiments using a Str mutant no. 3 (str-1) (FERM BP-08462) as the host. As expected, strain no. 3, which carries the plasmid pYI433 containing the wild-type rpsL gene, exhibited levels of Str about the same as wild-type levels (100–200 μg ml$^{-1}$). In parallel, the plasmid containing the rpsL gene significantly reduced the 4HBA-tolerance of the host when compared with strain no. 3 harbouring a plasmid without rpsL (1% versus 1.6%), demonstrating that str-1 mutation is responsible for the elevated tolerance to 4HBA.

Development of the 4HBA Tolerance by Sequential Adaptation

Figure 1:
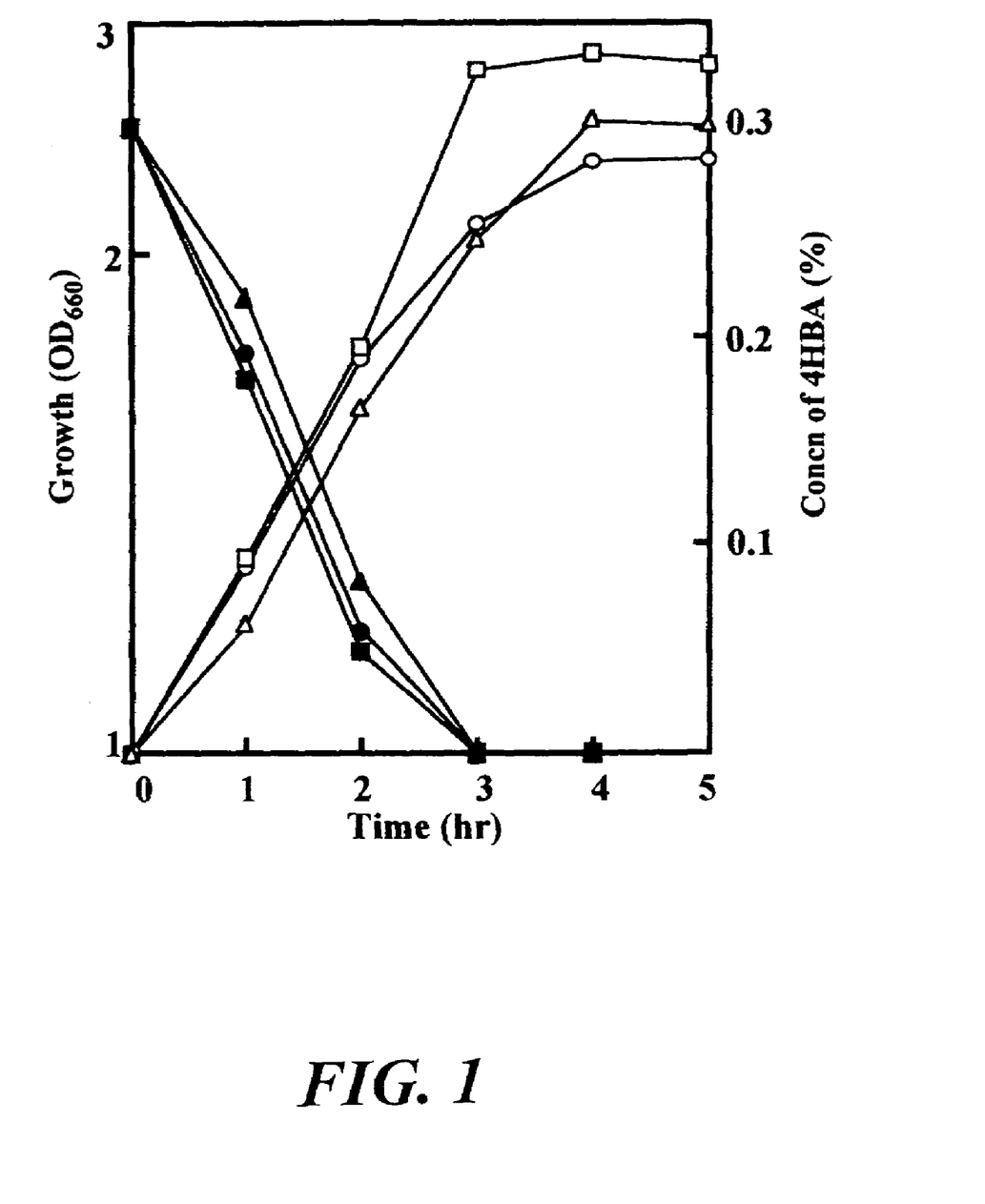
FIG. 1. Growth and consumption of 4HBA by *P. putida* wild-type and mutant strains. The strains were grown to mid-log phase in HBM medium containing 0.3% 4HBA, harvested by centrifugation and resuspended in the same medium to initially give $OD_{600}=1.0$ and then incubated on a reciprocal shaker. Open symbols show growth, while closed symbols show the concentration of 4HBA. Circle, wild-type KH146-2; square, Str mutant no. 3; triangle, Rif mutant no. 17.

To verify the significance of Str, Gen, and Rif mutations for the development of tolerance, we next attempted an opposite approach. Namely, we assumed that Str, Gen, and Rif phenotypes might appear in 4HBA-tolerant mutants, which were generated as described in the Experimental procedures. Thus, we first conferred a high level of tolerance by adapting the wild-type cells step by step to increasing concentrations of 4HBA (Table 4). At certain concentrations, 4HBA-tolerant colonies were isolated, and eventually we could obtain mutants that were highly tolerant (up to 5%) to 4HBA. Then, we examined these adapted tolerant cells for resistance to antibiotics. Strikingly, Str, Gen, and Rif traits all appeared at a frequency of 7 to 25% displaying the mutations in rpsL and/or rpoB genes (data not shown), when the screening concentration for 4HBA was 2.9% or 4.3% (Table 4). When 4HBA was up to 5%, the tolerant isolates all acquired the Str and Gen phenotypes. In contrast, the Rif phenotype was no longer detected, and the lack of mutation in the rpoB gene was confirmed by DNA sequencing. These Metabolic Activity of 4HBA Tolerant Mutants Strains no. 3 (FERM BP-08462) and no. 17 (FERM BP-08464) were chosen for further study as representative Str and Rif mutants, respectively. The growth rate as well as the consumption rate of 4HBA by the mutants were similar to the wild-type strain (FIG. 1). Furthermore, the wild-type and mutant strains both exhibited virtually the same activity for 4HBA 3-hydroxylase, the first enzyme in the 4HBA degradation pathway (data not shown). Also, no difference in degree of suppression of protein synthesis (see Experimental procedures) was detected between the wild-type and mutant strains when grown in the absence or presence (0.6 or 1.2%) of 4HBA (data not shown). These results indicate that the increased 4HBA-tolerance is not a result of the enhancement of metabolic activities or the development of tolerance in protein synthesis machinery (i.e. ribosome).

Uptake of 4HBA by Mutant Cells

Figure 2:
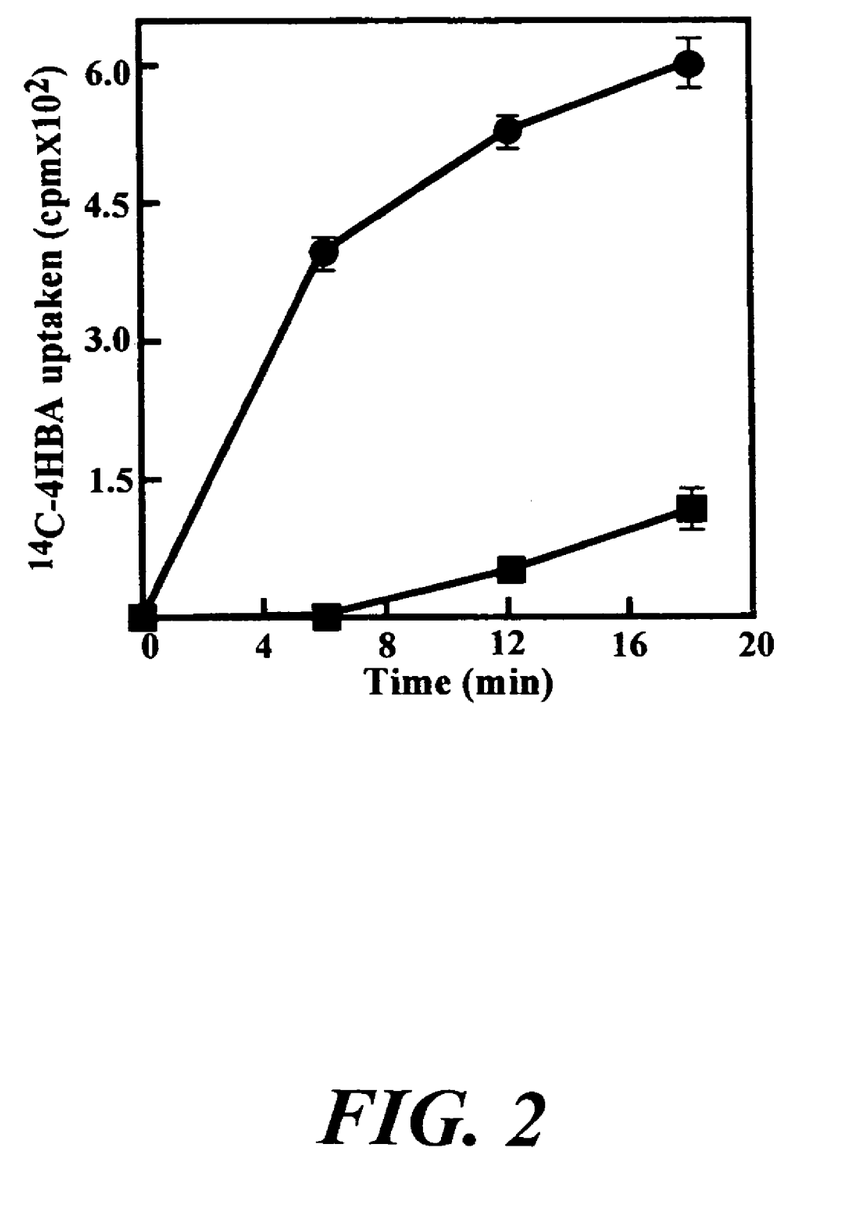
FIG. 2. Uptake of 4HBA by the wild-type strain of *P. putida* which was previously grown with either 0.3% 4HBA (●) or 0.3% succinate (■). Uptake of [$^{14}C$]4HBA was measured as described in Experimental procedures, and the mean values of two separate experiments are shown. Error bars represent the standard deviation.
Figure 3:
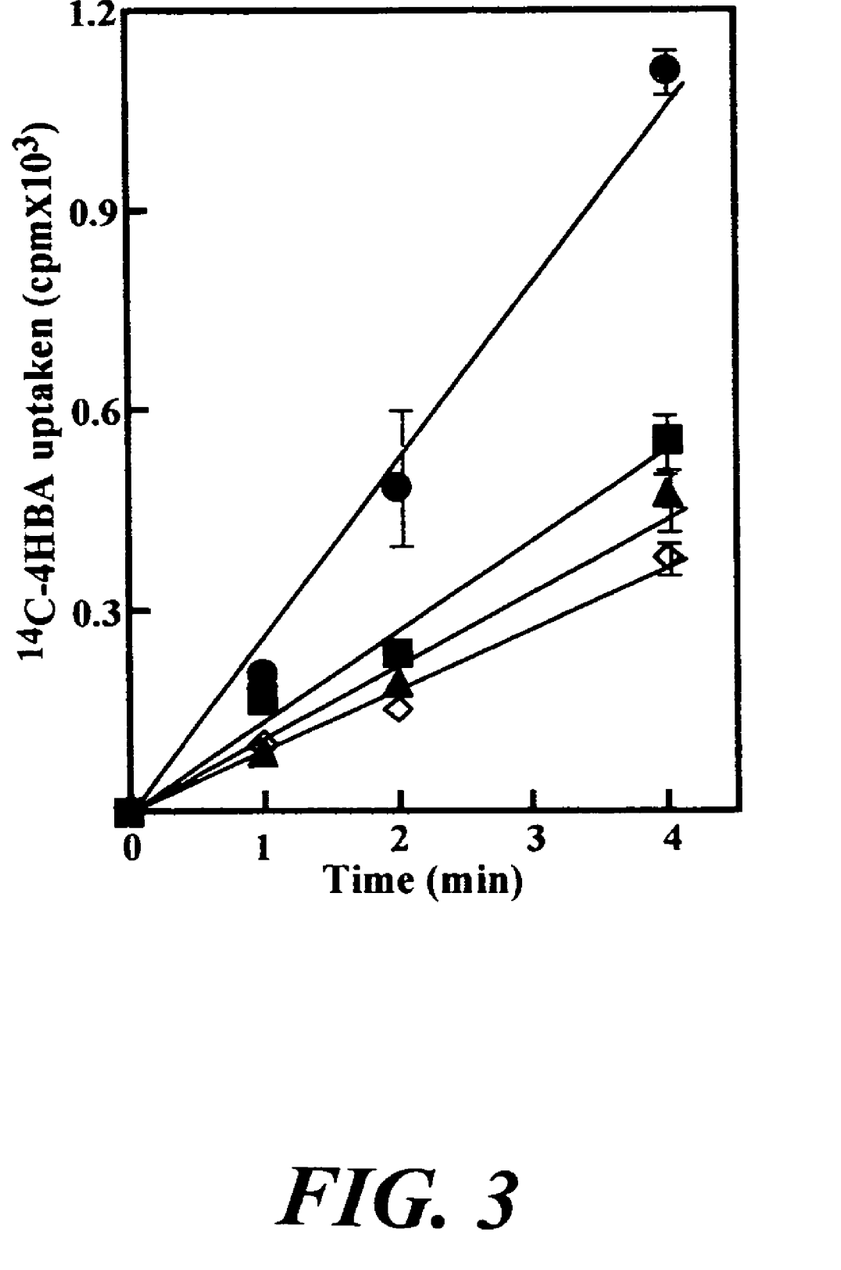
FIG. 3. Uptake of 4HBA by the wild type and mutant strains of *P. putida*. The strains were grown in HBM medium containing 0.3% 4HBA as the sole carbon source, and then uptake of [$^{14}C$]4HBA was measured as described in Experimental procedures. Error bars represent the standard deviation of the mean of triplicate samples. ●, wild-type KH146-2; ■, Str mutant no. 3; ▲, Rif mutant no. 17; ◊, Str Gen mutant no. 55.

To further investigate the mechanism of tolerance, we conducted experiments for uptake of 4HBA. In preliminary experiments, we found that the uptake of 4HBA is inducible. Cells which had previously grown in media with 4HBA as the sole carbon source consumed [$^{14}$C]4HBA efficiently, while the cells grown in media with succinate did not consume any [$^{14}$C]4HBA at least for the initial short term (FIG. 2). Later, [$^{14}$C]4HBA uptake was detectable, but not efficiently (FIG. 2), in agreement with the previous observation that induction of 4HBA 3-hydroxylase by addition of 4HBA requires 20 min (Hosokawa, 1970). Therefore, we first grew cells to mid-log phase in HBM medium containing 0.3% 4HBA and succinate, washed, and resuspended in HBM medium containing only succinate. [$^{14}$C]4HBA was then added with unlabeled 4HBA at various (50 to 500 μM) concentrations. The time course for uptake of [$^{14}$C]4HBA at 100 μM by the wild-type and mutant strains is shown in FIG. 3. The apparent Km value thus obtained was 240 μM for wild-type strain and the Str and Rif mutants displayed 2 to 3-fold greater Km values (470 μM for the Str mutant, and 620 μM for the Rif mutant). Likewise, the Str Gen double mutant no. 55, an isolate with a high level of tolerance, also revealed a reduced uptake for 4HBA (FIG. 3). Similar results were obtained when the uptake experiment was carried out by adjusting the culture medium to pH 8.0 instead of 6.8 (data not shown). Thus, the lowered uptake observed in mutants can be inferred to be a cause, at least in part, for the increased tolerance to 4HBA.

We have developed a new approach for improving the tolerance of bacterial cells to aromatic chemicals by introducing specified mutations or by adapting the cells sequentially to higher concentrations of 4HBA. The efficacy of Str, Gen and/or Rif mutations for activating or enhancing the secondary metabolism (i.e. antibiotic production) has been reported for *Streptomyces, Bacillus,* and *Pseudomonas* (Hosoya et al., ((1998) *Antimirob Agents Chemother* 42:2041–2047); Hu and Ochi, ((2001) *Appl Environ Microbiol* 67:1885–1892); Hu et al., ((2002) *J Bacteriol* 184: 3984–3991); Xu et al., ((2002) *Mol Genet Genom,* 268: 179–189)). Introducing Str mutation into *Pseudomonas pyrrocinia* gives rise to 10-fold increase in the production of the antibiotic pyrrolnitrin (Hosoya et al., ((1998) *Antimirob Agents Chemother* 42:2041–2047)). Thus, the Str mutation is effective not only for enhancing antibiotic production but for elevating the chemical tolerance in *Pseudomonas,* demonstrating that mutations in a ribosome or RNA polymerase endow the cell with an increased tolerance to aromatic chemicals. Particularly noteworthy is the fact that the high level (5%) 4HBA-tolerant strains isolated after sequential adaptation all possessed a rpsL mutation (str-1), which altered Lys-88 to Arg, implicating strongly the significance of the str-1 mutation for development of high level tolerance. The Gen mutation, though not identified, is also likely to be an essential trait for high level tolerance (Table 4).

The action of streptomycin on bacterial ribosomes has been studied in great detail (reviewed by Wallace et al., ((1979) Streptomycin and related antibiotics. In *Antibiotics V-mechanism of action of antibacterial agents.* F. E. Hahn (ed.), Springer-Verlag, New York, N.Y. pp. 272–303) and Cundliffe, ((1990) Recognition sites for antibiotics within rRNA. In *The ribosome: structure, function, and evolution.* W. E. Hill, A. Dahlberg, R. A. Garrett, P. B. Moore, D. Schlessinger, and J. R. Warner (eds.), American Society for Microbiology, Washington, D.C. pp. 479–490)), and among the numerous effects attributed to this drug, the misreading of the mRNA codons is the best known. Resistance to streptomycin has been shown to result from a limited number of point mutations in the rpsL gene, which encodes the ribosomal protein S12. The previously reported amino acid positions in which changes conferred streptomycin resistance in *E. coli, B. subtilis* and *Mycobacterium tuberculosis* are Lys-43, Lys-88, and Pro-91 (Finken et al., ((1993) *Mol Microbiol* 9:1239–1246.); Honore and Cole, ((1994) *Antimicrob Agents Chemother* 38:238–242); Inaoka et al., ((2001) *J Bacteriol* 183:4958–4963); Meier et al., ((1994) *Antimicrob Agents Chemother* 38:228–233)). In the present study, alterations found in the two sites (Lys-43 and Lys-88) therefore represent previously known positions (Table 3). Gentamicin belongs to the kanamycin class of aminoglycosides but is different from streptomycin when classified on the basis of structural characteristics. Exact mutation points for the Gen mutants remain undetected in our present study, although a certain gentamicin resistance has been shown to result from a mutation in the rplF gene, which codes for the ribosomal L6 protein (Buckel et al., ((1977) *Mol Gen Genet* 158:47–54); Kuhberger et al., ((1979) *Biochemistry* 18:187–193)). Previous studies dealing with various bacteria have indicated that mutations in the rpoB gene, which encodes the β-subunit of RNA polymerase, are responsible for the acquisition of resistance to rifampicin (Heep et al., ((1999) *Antimicrob Agents Chemother* 43:1497–1499); Jin and Gross, ((1988) *J Mol Biol* 202:45–58); Singer et al., ((1993) *J Mol Biol* 231:1–5); Wichelhaus et al., ((1999) *Antimicrob Agents Chemother* 43:2813–2816)). Almost all the mutations found are located on a specified conserved region of the rpoB gene that can be divided into three clusters (Jin and Gross, 1988). In the present study, all of the Rif mutants examined exhibited a point mutation in clusters I or II (Table 3). It is conceivable that the altered conformational status of the RNA polymerase which may result from a rif mutation can give rise to different promoter selectivity (or affinity), directly or indirectly leading to a different level of expression for each gene. Indeed, as demonstrated in *E. coli,* the mutant RNA polymerase may have altered promoter selectivity (Ishihama et al., (1990) Structural and Functional modulation of *Escherichia coli* RNA polymerase. In *Structure and function of nucleic acids and proteins.* Felicia Y., H. Wu and Cheng W. W. (eds.), Raven Press, New York. pp. 153–159.). Although the molecular basis of these str, gen, and rif mutations for the increased tolerance to aromatic chemicals remains obscure, it is apparent that these mutations ultimately cause physiological changes in the membrane, resulting in reduced permeability as demonstrated using [$^{14}$C] 4HBA (FIG. 3). This result may explain a part of the increased tolerance.

Gram negative bacteria, including *Pseudomonas,* have a complex membrane system consisting of an outer membrane, an inner membrane, and a periplasmic space (reviewed by Sikkema et al., (1995) *Microbiol Rev* 59:201–202). Solvent tolerance could be achieved, 1) by reducing the rate of uptake through outer membrane, 2) by increasing the rate of metabolism of the ingested compound, or 3) by increasing the rate of the energy-coupled efflux pump consisting of several kinds of tripartite protein complexes (Aono et al., ((1998) *J Bacteriol* 180:938–944); Nikaido, ((1996) Multidrug efflux pumps of Gram negative bacteria. *J Bacteriol* 178:5853–5859); Ramos et al., (1998) *J Bacteriol* 180:3323–3329)). It is also possible that 4HBA damage may be exerted at the level of the outer membrane in an effect independent from the metabolism of the compound. Different mechanisms contributing to the solvent tolerance have been found. First, adaptive changes in the composition of the inner and outer membranes have been described. These alterations in the membrane structure suppress the effects of the solvents on membrane stability or limit the rate of diffusion through the membrane. Ramos-González et al. ((2001) *Appl Environ Microbiol* 67:4338–4341) demonstrated that *P. putida* DOT-T1E exposed to a high concentration (1.5%) of 4HBA caused cis-to-trans isomerization of unsaturated fatty acids in the membrane lipid. In addition to these adaptation mechanisms, there exist efflux systems that actively decrease the amount of the toxic solvent in the cells (Huertas et al., ((2000) *Environ Sci Technol* 34: 3395–3400); Kim et al., ((1998) *J Bacteriol* 180:3692–3696); Nishimo and Yamaguchi, ((2001) *J Bacteriol* 183: 5803–12); reviewed by Isken and de Bont, ((1998) *Extremophiles* 2:229–238)). Multidrug active efflux systems have recently been recognized as efficient mechanisms for organic solvent resistance in *P. aeruginosa* (Aires et al., ((1999) *Antimicrob Agents Chemother* 43:2624–2628); Li et al., ((1998) *J Bacteriol* 180:2987–2991); Mine et al., ((1999) *Antimicrob Agents Chemother* 43:415–417)), *P. putida* (Kieboom et al., ((1998) *J Bacteriol* 180:6769–6772); Kieboom and de Bont, ((2001) *Microbiology* 147:43–51); Rojas et al., ((2001) *J Bacteriol* 183:3967–3973)), and in *E. coli* (Nishino and Yamaguchi, ((2001) *J Bacteriol* 183: 5803–12); White et al., ((1997) *J*

Bacteriol 179:6122–6126)). The system contributes also to the energy-dependent efflux of a wide variety of antimicrobial agents, including streptomycin and rifampicin (Kieboom and de Bont, ((2001) *Microbiology* 147:43–51); Mine et al., ((1999) *Antimicrob Agents Chemother* 43:415–417); Nishino and Yamaguchi, ((2001) *Mol Microbiol* 40:917–931)). Therefore, one may suppose that the drug resistant mutants used here have inadvertently developed additional mutation(s) in an element involved in the efflux system. This possibility, however, can be ruled out, since the rpsL mutation was proved to be responsible for the enhanced tolerance to 4HBA (see Results). In this light, the work described by Harwood et al. (1994) may be significant. In *P. putida*, the pcaK gene product is a transporter ptotein for 4HBA with a deduced amino acid sequence indicative of membership in the major facilitator superfamily of transport proteins. pcaK mutants have been shown to accumulate 4HBA at reduced rates (Harwood et al., ((1994) *J Bacteriol* 176:6479–6488)). Thus, it is possible that our Str, Gen, and Rif mutations repressed (by an entirely unknown mechanism) the expression of pcaK gene, resulting in the reduced uptake of 4HBA. Alternatively, since the apparent uptake rate is the sum of the actual uptake (influx) and efflux, it is also possible that these drug resistant mutants have acquired a capacity to overproduce wide-specificity efflux pumps by somehow enhancing the expression of the key genes (such as marA, mexAB, mexXY, srpABC, ttgABC, ttgDEF etc.) that play a role in the efflux system. If this is the case, the slower permeation of 4HBA into mutant cells (FIG. 3) may be a balance between unaltered influx and increased efflux. Our present findings might help in elucidating the mechanisms of tolerance to toxic organic chemicals particularly its relationship with transcription and translation machinery, although further work is necessary to clarify this mechanism for tolerance. Efficacy of Str and Rif mutations for elevating the cell's tolerance to organic solvents such as toluene and xylene (see Results) implicates the widespread applicability of our method in improving the ability of microorganisms to process chemical wastes.

Obviously, numerous modifications and variations of the present invention are possible in light of the above teachings. It is therefore to be understood that within the scope of the appended claims, the invention may be practiced otherwise than as specifically described herein.

The invention claimed is:

1. An isolated *Pseudomonas putida* strain selected from the group consisting of FERM BP-08462, FERM BP-08463, FERM BP-08464, and FERM BP-08465.

2. The isolated *Pseudomonas putida* strain of claim 1, which is FERM BP-08462.

3. The isolated *Pseudomonas putida* strain of claim 1, which is FERM BP-08463.

4. The isolated *Pseudomonas putida* strain of claim 1, which is FERM BP-08464.

5. The isolated *Pseudomonas putida* strain of claim 1, which is FERM BP-08465.

6. A composition comprising the isolated *Pseudomonas putida* strain of claim 2 and a carrier.

7. A composition comprising the isolated *Pseudomonas putida* strain of claim 3 and a carrier.

8. A composition comprising the isolated *Pseudomonas putida* strain of claim 4 and a carrier.

9. A composition comprising the isolated *Pseudomonas putida* strain of claim 5 and a carrier.

10. A composition comprising one or more isolated *Pseudomonas putida* strain(s) selected from the group consisting of FERM BP-08462, FERM BP-08463, FERM BP-08464, and FERM BP-08465; and a carrier.

11. A method of detoxifying industrial wastes of toxic organic compounds, comprising contacting the industrial wastes with the *Pseudomonas putida* of claim 2 for a time to detoxify the industrial waste.

12. A method of detoxifying industrial wastes of toxic organic compounds, comprising contacting the industrial wastes with the *Pseudomonas putida* of claim 3 for a time to detoxify the industrial waste.

13. A method of detoxifying industrial wastes of toxic organic compounds, comprising contacting the industrial wastes with the *Pseudomonas putida* of claim 4 for a time to detoxify the industrial waste.

14. A method of detoxifying industrial wastes of toxic organic compounds, comprising contacting the industrial wastes with the *Pseudomonas putida* of claim 5 for a time to detoxify the industrial waste.

15. A method of detoxifying industrial wastes of toxic organic compounds, comprising contacting the industrial wastes with the composition of claim 10 for a time to detoxify the industrial waste.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 1
cgtaagacaa tcagtggagc                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 2
ccgaccttac tcttatcgac                                              20

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 3 aagaacccccg tcaagctcc                                              19

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 4
tctttacgac ggacgacttc                                              20

```
<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 5
tgatcaacgc caagccggt                                              19

<210> SEQ ID NO 6
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 6
ttgcgctcca tgccggtac                                              19

<210> SEQ ID NO 7
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 7
cgttttgccg ctacacgacg tcttggcat                                   29

<210> SEQ ID NO 8
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 8
aagagaacgt ggtcgtgggt cgtctgatc                                   29
```